(12) United States Patent
Florio et al.

(10) Patent No.: US 6,647,295 B2
(45) Date of Patent: Nov. 11, 2003

(54) IMPLANTABLE CARDIAC STIMULATION DEVICE WITH DETECTION AND THERAPY FOR PATIENTS WITH VASOVAGAL SYNCOPE

(75) Inventors: Joseph J. Florio, La Canada, CA (US); Gregory Hauck, Valencia, CA (US); Gene A. Bornzin, Simi Valley, CA (US)

(73) Assignee: PaceSetter, Inc., Sylmar, CA (US)

( * ) Notice: Subject to any disclaimer, the term of this patent is extended or adjusted under 35 U.S.C. 154(b) by 250 days.

(21) Appl. No.: 09/849,722

(22) Filed: May 3, 2001

(65) Prior Publication Data

US 2002/0004670 A1 Jan. 10, 2002

Related U.S. Application Data

(60) Provisional application No. 60/204,353, filed on May 15, 2000.

(51) Int. Cl.$^7$ .................................................. A61N 1/365
(52) U.S. Cl. .............................................. 607/9; 607/17
(58) Field of Search ............................... 607/2, 9, 17–19, 607/23–26

(56) References Cited

U.S. PATENT DOCUMENTS

| | | | |
|---|---|---|---|
| 4,535,774 A | 8/1985 | Olson ................... 128/419 PG |
| 4,562,841 A | 1/1986 | Brockway et al. ..... 128/419 PG |
| 4,856,523 A | 8/1989 | Sholder et al. ............. 128/419 |
| 4,955,376 A | 9/1990 | Callaghan et al. .......... 128/419 |
| 5,010,893 A | 4/1991 | Sholder ....................... 128/782 |
| 5,233,984 A | * 8/1993 | Thompson ................... 607/18 |
| 5,237,992 A | 8/1993 | Poore .......................... 607/18 |
| 5,269,299 A | 12/1993 | Duncan ................ 128/419 PG |
| 5,284,491 A | 2/1994 | Sutton et al. ................. 607/17 |
| 5,354,317 A | * 10/1994 | Alt .............................. 607/19 |
| 5,417,716 A | 5/1995 | Franberg et al. ............... 607/9 |
| 5,441,525 A | 8/1995 | Shelton et al. ................ 607/23 |
| 5,466,254 A | 11/1995 | Helland ....................... 607/123 |
| 5,501,701 A | 3/1996 | Markowitz et al. ............. 607/9 |
| 5,540,728 A | 7/1996 | Shelton et al. ................ 607/23 |
| 5,615,684 A | 4/1997 | Hagel et al. ................. 128/670 |
| 5,676,686 A | 10/1997 | Jensen et al. ................... 607/9 |
| 5,865,760 A | 2/1999 | Lidman et al. ............. 600/509 |
| 5,913,879 A | 6/1999 | Ferek-Petric et al. ......... 607/14 |
| 5,991,659 A | 11/1999 | De Vries et al. ................ 607/9 |
| 6,044,297 A | * 3/2000 | Sheldon et al. ............... 607/17 |
| 6,049,734 A | 4/2000 | Lang .............................. 607/9 |
| 6,049,735 A | 4/2000 | Hartley et al. .................. 607/9 |
| 6,351,672 B1 | * 2/2002 | Park et al. .................... 607/19 |
| 6,466,821 B1 | * 10/2002 | Pianca et al. ................. 607/18 |

OTHER PUBLICATIONS

Barold, S. Serge, et al., "Recent Advances in Cardiac Pacing" Goals for the 21$^{st}$ Century, Futura, 1997, pp. 92–95.
Benditt, David G. MD, et al., "Cardiac Pacing for Prevention of Recurrent Vasovagal Syncope", Ann Intern Med., 1995, 122 pp. 204–209.

* cited by examiner

Primary Examiner—Angela D. Sykes
Assistant Examiner—Kristen Droesch

(57) ABSTRACT

A pacemaker or other implantable cardiac stimulation device is configured with both a rate hysteresis mode and a vasovagal syncope prevention mode. Within the rate hysteresis mode, the pacemaker detects when the intrinsic heart rate of the patient is below an escape rate, then paces the heart at a Base Rate until an intrinsic beat is detected. When programmed in the vasovagal syncope prevention mode, upon detecting the intrinsic rate falling below the Hysteresis Escape Rate, the pacemaker paces the heart at a Vasovagal Syncope Response Rate, which is considerably higher than the Base Rate. The pacemaker is preferably set to the syncope prevention mode for patients prone to recurrent vasovagal syncope. By pacing the heart at the higher Vasovagal Syncope Response Rate, the pacemaker thereby helps prevent a significant drop in blood pressure which might otherwise cause a loss of consciousness in the patient. System and method embodiments are described.

22 Claims, 2 Drawing Sheets

IMPLANTABLE CARDIAC STIMULATION DEVICE WITH DETECTION AND THERAPY FOR PATIENTS WITH VASOVAGAL SYNCOPE

PRIORITY CLAIM

This application claims the benefit of U.S. provisional application Ser. No. 60/204,353, filed May 15, 2000.

FIELD OF THE INVENTION

The invention generally relates to cardiac pacing techniques and in particular to techniques for preventing vasovagal syncope using cardiac pacing.

BACKGROUND OF THE INVENTION

Syncope is a sudden loss of strength or consciousness caused by reduced cerebral circulation, itself typically the result of vasodilation. Vasovagal syncope is a type of syncope referred to as a neurocardiogenic syncope wherein the syncope is triggered by an interaction between the heart and nerve tissue connected to the heart. Neurocardiogenic syncope may also be referred to as neuromediated syncope, neurally mediated syncope, cardioinhibitory syncope, cardioneurogenic syncope, vasodepressor syncope, malignant vasovagal syndrome, neurally mediated hypotension/bradycardia and cardiovascular neurogenic syncope. For vasovagal syncope, the interaction occurs between the heart and the vagus nerve.

Evidence suggests that vasovagal syncope is initially triggered by a sudden reduction in peripheral vascular resistance, perhaps resulting from stress, pooling of blood in the extremities, or other factors. As a result of the reduction in peripheral vascular resistance, the pressure of blood entering the heart drops and the amount of blood filling the ventricles prior to ventricular contractions therefore also drops. With less blood in the ventricles, the ventricles thereby contract much more quickly and vigorously than would otherwise occur in an effort to maintain a constant stroke volume. The more vigorous ventricular contractions have the effect of stimulating ventricular mechanoreceptors, also known as C fibers, that normally only respond to ventricular expansion or stretching, rather than contraction. The activation of the ventricular mechanoreceptors results in a surge in neural traffic to the brainstem, particularly to the nucleus tractus solitaries, via the vasovagal nerve.

For most people, the neurological system properly interprets the increase of activity of the mechanoreceptors as being in response to a drop in peripheral vascular resistance and compensates by increasing the heart rate and constricting the blood vessels. However, in certain patients, as a result of a neurological condition within the vagus nerve or for some other reason, the surge in neural traffic is falsely perceived by the neurological system as being representative of hypertension. In response thereto, the brainstem triggers an increase in peripheral vasodilation and a reduction in heart rate. The vasodilation and the drop in heart rate, in turn, cause a still further reduction in blood pressure, i.e. hypotension. In other words, the actions taken by the brainstem exacerbate the problem. If the degree of hypotension is sufficiently severe, cerebral hypoperfusion occurs wherein brain cells do not receive enough oxygen and, consequently, the victim loses consciousness. Accordingly, within these patients, any sudden drop in peripheral vascular resistance can trigger vasovagal syncope and the patients suffer from recurrent vasovagal syncope. Further information regarding vasovagal syncope may be found in S. Serge Barold and Jacques Mugica, *Recent Advances in Cardiac Pacing*, Futura Publishing Company, 92–95, 1997.

As can be appreciated, loss of consciousness can be particularly dangerous for the patient if occurring while the patient is driving a motor vehicle, climbing a flight of stairs or engaged in any other activity wherein the loss of consciousness could result in injury or death. Accordingly, it is highly desirable to provide techniques for preventing vasovagal syncope or other forms of neurocardiological syncope. One possible technique for preventing vasovagal syncope is to employ a pacemaker, or other implantable cardiac stimulation device, to pace the heart to prevent the reduction in blood pressure associated with vasovagal syncope from occurring. Indeed, the American College of Cardiology-American Heart Association suggested in 1991 that vasovagal syncope in patients should be used as a Class 2 indication for pacing therapy. However, conventional cardiac pacemakers have had only limited success in preventing recurrent vasovagal syncope. (See David G. Benditt et al., *Cardiac Pacing for Prevention of Recurrent Vasovagal Syncope*, Ann Intern Med. 1995; 122; 204–209.)

With many conventional techniques for preventing vasovagal syncope, the cardiac pacemaker analyzes a sequence of intrinsic heart beats (i.e. natural or non-stimulated heart beats) to determine whether the sequence of heart beats indicates an episode of vasovagal syncope and, if so, the pacemaker paces the heart. In one example, if the intrinsic heart rate falls below a lower threshold, the pacemaker then analyzes the immediately preceding heart beats to determine whether a sharp drop in heart rate has occurred. If so, the pacemaker then continues to monitor intrinsic heart beats to determine whether the heart rate remains at a stable rate below the threshold rate. If the rate remains stable for a predetermined number of heart beats, the pacemaker then concludes that an episode of vasovagal syncope may be occurring and begins pacing at an elevated heart rate. Unfortunately, by the time the pacemaker has had the opportunity to analyze a sufficient number of heart beats to determine whether an episode of vasovagal syncope is occurring, the blood pressure of the patient has likely dropped to the point where an elevated heart rate will not remedy the vasovagal syncope and the patient will become unconscious. In this regard, the drop in blood pressure results in significantly less blood filling the ventricles, such that there is simply not enough incoming blood to pump. Hence, overall blood pressure is not significantly increased merely by pumping the heart faster, and the aforementioned cerebral hypoperfusion still occurs resulting in unconsciousness. Indeed, depending upon the programming of the pacemaker, it may take five to eight seconds or more before the pacemaker begins increasing the heart rate.

Moreover, vasovagal syncope detection techniques, which require analysis of numerous heart beats, can be fairly elaborate thereby requiring considerable computing resources, particularly memory space. Within many pacemaker or implantable cardioverter defibrillator (ICD) designs, all or most of the available processing resources are devoted to pre-existing software programs. Examples include programs for: detecting ventricular and atrial arrhythmias and administering responsive therapy; performing automatic mode switch operations between an atrial tracking mode and a non-atrial tracking mode; monitoring the battery or other power supply; and storing diagnostic information such as a list of pacing events along with the internal electrocardiogram (IEGM). Another example is a rate hysteresis program that temporarily paces the heart at a Base Rate whenever the intrinsic heart rate falls below a Hysteresis Escape Rate so as to permit the heart to typically beat with an intrinsic heart rhythm as opposed to a paced rhythm. In addition to these examples, many, many other programs are usually provided in state of the art stimulation devices, typically consuming most or all available computing resources. Hence, to add a complex vasovagal syncope detection algorithm, the stimulation device may need to be re-designed to provide additional computing resources, such as a more powerful processor, larger memory system or faster bus system. Moreover, even if the hardware of the stimulation device need not be modified, additional costs will arise in the design, development and de-bugging of the complex vasovagal syncope detection software.

Accordingly, it would be highly desirable to provide an improved cardiac stimulation device capable of promptly pacing the heart at an elevated rate upon detection of possible vasovagal syncope, so as to prevent a significant drop in blood pressure to thereby more effectively prevent loss of consciousness. It would also be highly desirable to provide an improved cardiac stimulation device capable of detecting and responding to a possible episode of vasovagal syncope without requiring complex vasovagal analysis software consuming considerable processing resources. It is to these ends that aspects of the present invention are primarily directed.

SUMMARY OF THE INVENTION

In accordance with one aspect of the invention, a method is provided for pacing the heart using an implantable cardiac stimulation device wherein the device can operate vasovagal syncope prevention mode by detecting a sudden decrease in rate below a predetermined rate threshold below the Base Rate, referred to herein as the "Hysteresis Escape Rate." As used herein, a "prevention mode" serves to quickly detect and immediately compensate for the sudden drop in intrinsic heart rate so that the patient does not experience loss of consciousness.

In another embodiment, the stimulation device can operate in either a rate hysteresis pacing mode or a vasovagal syncope prevention mode, since both operate using the Hysteresis Escape Rate. The desired mode may be pre-programmed into the device by the physician, or in an alternate embodiment, can be determined by the device using various physiologic or position sensors.

The stimulation device monitors the intrinsic heart rate of the patient and determines whether the intrinsic rate has fallen below a predetermined Hysteresis Escape Rate. Within the rate hysteresis mode, if the intrinsic heart rate falls below the escape rate, the stimulation device paces the heart at a predetermined Base Rate. In the vasovagal syncope prevention mode, if the intrinsic heart rate falls below the escape rate, the stimulation device paces the heart at a Vasovagal Syncope Response Rate, which is greater than the Base Rate. The Vasovagal Syncope Response Rate is preferably set sufficiently high to offset the drop in blood pressure associated with vasovagal syncope to thereby reduce the risk of loss of consciousness by the patient.

In this manner, patients susceptible to vasovagal syncope can have their pacemaker, ICD or other implantable cardiac stimulation device programmed to the vasovagal syncope prevention mode wherein the pacemaker, upon detecting a possible episode of vasovagal syncope as indicated by the intrinsic heart rate falling below the escape rate, immediately begins pacing at the Vasovagal Syncope Response Rate set in an effort to prevent loss of consciousness by the patient. This is in contrast to the conventional techniques discussed above wherein the pacemaker analyzes numerous heart beats following a drop in heart rate before determining whether an episode of vasovagal syncope is occurring and, only then, increases the heart rate. As noted, by the time the heart rate is increased, the blood pressure may have dropped to the point where the increase in stimulation rate is ineffective to prevent loss of consciousness. Another advantage of the technique of the invention is that it requires only relatively minor modifications to otherwise conventional rate hysteresis pacing programs. Hence the invention can be easily, inexpensively and reliably implemented, even within pacemaker designs having limited additional processing resources, such as limited unused memory space.

In an exemplary embodiment, the Base Rate and Vasovagal Syncope Response Rate are both fixed programmable values. In other embodiments, the Vasovagal Syncope Response Rate is determined by periodically detecting a peak average intrinsic ventricular rate (determined by a moving average of several ventricular cardiac cycle durations) and setting the Vasovagal Syncope Response Rate to at least the latest detected peak average rate. The peak average rate may be detected, for example, once every minute based on the preceding minute or may be detected based upon the intrinsic rate over a preceding fixed number of pacing cycles, such as sixty-four cycles.

Advantageously, the date and time of the initiation of each period of pacing at the Vasovagal Syncope Response Rate is recorded for a later review by a physician. The pacemaker paces the heart at the Vasovagal Syncope Response Rate for a programmable number of cycles or a predetermined period of time, then begins incrementally decreasing the stimulation rate until it resumes operation at base rate.

Apparatus embodiments of the invention are also provided. Other features, advantages and aspects of the invention are either described below or will be apparent from the descriptions below in combination with the accompanying drawings.

BRIEF DESCRIPTION OF THE DRAWINGS

Further features and advantages of the invention may be more readily understood by reference to the following description taken in conjunction with the accompanying drawings, in which.

DETAILED DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
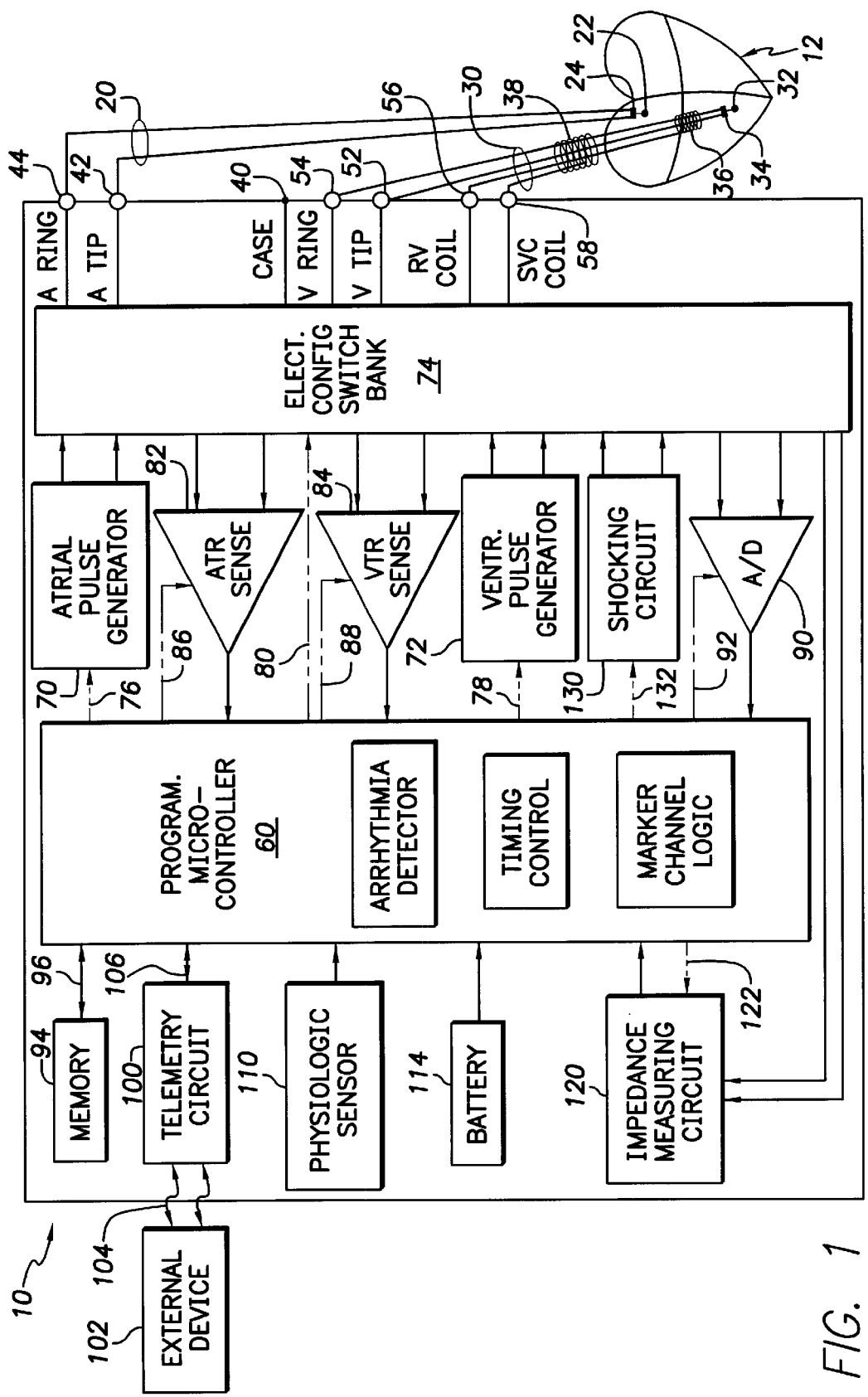
FIG. 1 is a functional block diagram of a dual-chamber implantable stimulation device illustrating the basic elements of a stimulation device which can provide cardioversion, defibrillation and pacing stimulation and which can be programmed to a vasovagal syncope prevention mode in accordance with an exemplary embodiment of the invention.

In FIG. 1, a simplified block diagram is shown of a dual-chamber implantable stimulation device 10 which is capable of treating both fast and slow arrhythmias with stimulation therapy, including cardioversion, defibrillation, and pacing stimulation. While a dual-chamber device is shown, this is for illustration purposes only, and one of skill in the art could readily eliminate or disable the appropriate circuitry to provide a single-chamber stimulation device capable of treating one chamber with cardioversion, defibrillation and pacing stimulation.

To provide atrial chamber pacing stimulation and sensing, the stimulation device 10 is shown in electrical communication with a patient's heart 12 by way of an implantable atrial lead 20 having an atrial tip electrode 22 and an atrial ring electrode 24 which typically is implanted in the patient's atrial appendage.

The stimulation device 10 is also shown in electrical communication with the patient's heart 12 by way of an implantable ventricular lead 30 having, in this embodiment, a ventricular tip electrode 32, a ventricular ring electrode 34, a right ventricular (RV) coil electrode 36, and an SVC coil electrode 38. Typically, the ventricular lead 30 is transvenously inserted into the heart 12 so as to place the RV coil electrode 36 in the right ventricular apex, and the SVC coil electrode 38 in the superior vena cava. Accordingly, the ventricular lead 30 is capable of receiving cardiac signals, and delivering stimulation in the form of pacing and shock therapy to the right ventricle.

While only two leads are shown in FIG. 1, it is to be understood that additional stimulation leads (with one or more pacing, sensing and/or shocking electrodes) may be used in order to efficiently and effectively provide pacing stimulation to the left side of the heart or atrial cardioversion and/or defibrillation. For example, a lead designed for placement in the coronary sinus region could be implanted to deliver left atrial pacing, atrial shocking therapy, and/or for left ventricular pacing stimulation. For a complete description of a coronary sinus lead, see U.S. patent application No. 09/457,277, filed Dec. 8, 1999, titled "A Self-Anchoring, Steerable Coronary Sinus Lead" (Pianca et al.), which is a continuation-in-part of U.S. patent application Ser. No. 09/196,898, filed Nov. 20, 1998 (now abandoned); and U.S. Pat. No. 5,466,254, "Coronary Sinus Lead with Atrial Sensing Capability" (Helland), which patents are hereby incorporated herein by reference.

The housing 40 (shown schematically) for the stimulation device 10 includes a connector (not shown) having an atrial pin terminal 42 and an atrial ring terminal 44, which are adapted for connection to the atrial tip electrode 22 and the atrial ring electrode 24, respectively. The housing 40 further includes a ventricular pin terminal 52, a ventricular ring terminal 54, a ventricular shocking terminal 56, and an SVC shocking terminal 58, which are adapted for connection to the ventricular tip electrode 32, the ventricular ring electrode 34, the RV coil electrode 36, and the SVC coil electrode 38, respectively. The housing 40 (often referred to as the "can", "case" or "case electrode") may be programmably selected to act as the return electrode, or anode, alone or in combination with one of the coil electrodes, 36 and 38. For convenience, the names of the electrodes are shown next to the terminals.

At the core of the stimulation device 10 is a programmable microcontroller 60, which controls the various modes of stimulation therapy. As is well known in the art, the microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions is well known in the art.

As shown in FIG. 1, an atrial pulse generator 70 and a ventricular pulse generator 72 generate pacing stimulation pulses for delivery by the atrial lead 20 and the ventricular lead 30, respectively, via a switch bank 74. The pulse generators, 70 and 72, are controlled by the microcontroller 60 via appropriate control signals, 76 and 78, respectively, to trigger or inhibit the stimulation pulses. The microcontroller 60 further includes timing circuitry that controls the operation of the stimulation device timing of such stimulation pulses that is well known in the art.

The switch bank 74 includes a plurality of switches for switchably connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar or bipolar) by selectively closing the appropriate combination of switches (not shown) as is known in the art.

An atrial sense amplifier 82 and a ventricular sense amplifier 84 are also coupled to the atrial and ventricular leads 20 and 30, respectively, through the switch bank 74 for detecting the presence of cardiac activity. The switch bank 74 determines the "sensing polarity" of the cardiac signal by selectively closing the appropriate switches, as is also known in the art. In this way, the clinician may program the sensing polarity independent of the stimulation polarity.

Each sense amplifier, 82 and 84, preferably employs a low power, precision amplifier with programmable gain and/or automatic gain control, band pass filtering, and a threshold detection circuit, known in the art, to selectively sense the cardiac signal of interest. The automatic gain control enables the device 10 to deal effectively with the difficult problem of sensing the low frequency, low amplitude signal characteristics of ventricular fibrillation.

The outputs of the atrial and ventricular sense amplifiers, 82 and 84, are connected to the microcontroller 60, which, in turn, inhibit the atrial and ventricular pulse generators, 70 and 72, respectively, in a demand fashion whenever cardiac activity is sensed in the respective chambers.

For arrhythmia detection, the present device utilizes the atrial and ventricular sense amplifiers, 82 and 84, to sense cardiac signals to determine whether a rhythm is physiologic or pathologic. As used herein "sensing" is reserved for the noting of an electrical depolarization, and "detection" is the processing of these sensed depolarization signals and noting the presence of an arrhythmia. The timing intervals between sensed events (e.g., the P—P and R—R intervals) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, also known as "tiered therapy").

Cardiac signals are also applied to the inputs of an analog to digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the atrial and ventricular leads, 20 and 30, through the switch bank 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart 28 within each respective tier of therapy.

Advantageously, the operating parameters of the implantable device 10 may be non-invasively programmed into the memory 94 through a telemetry circuit 100 in telemetric communication with an external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through the established communication link 104.

In the preferred embodiment, the stimulation device 10 further includes a physiologic sensor 110. Such sensors are commonly called "rate-responsive" sensors. The physiological sensor 110 is used to detect the exercise state of the patient, to which the microcontroller 60 responds by adjusting the rate and AV Delay at which the atrial and ventricular pulse generators, 70 and 72, generate stimulation pulses.

In one embodiment, the present invention includes a physiological sensor 110 that is capable of detecting vasovagal syncope. Accordingly, a "vasovagal syncope detecting sensor" would include any sensor that could detect hypotension, cerebral hypoperfusion, or loss of consciousness, as will be discussed in more detail below.

The stimulation device additionally includes a battery 114, which provides operating power to all of the circuits shown in FIG. 1. For the stimulation device 10, which employs shocking therapy, the battery must be capable of operating at low current drains for long periods of time and then be capable of providing high-current pulses (for capacitor charging) when the patient requires a shock pulse. The battery 114 must also have a predictable discharge characteristic so that elective replacement time can be detected. Accordingly, the device employs lithium/silver vanadium oxide batteries, as is true for most (if not all) such devices to date.

If the present invention is employed in an ICD, it must detect the occurrence of an arrhythmia, and automatically apply an appropriate electrical shock therapy to the heart aimed at terminating the detected arrhythmia. To this end, the microcontroller 60 further controls a shocking circuit 130 by way of a control signal 132. The shocking circuit 130 generates shocking pulses of low (up to 0.5 Joules), moderate (0.5–10 Joules), or high energy (11 to 40 Joules), as controlled by the microcontroller 60. Such shocking pulses are applied to the patient's heart through at least two shocking electrodes, and as shown in this embodiment, using the RV and SVC coil electrodes, 36 and 38, respectively. In alternative embodiments, the housing 40 may act as an active electrode in combination with the RV electrode 36 alone, or as part of a split electrical vector using the SVC coil electrode 38 (i.e., using the RV electrode as common).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

In one embodiment, the device 10 is configured to operate in either a standard rate hysteresis mode or a vasovagal syncope prevention mode. In either mode, the controller 60 monitors the intrinsic heart rate of the patient and detects whether the intrinsic rate has fallen below a preprogrammed Hysteresis Escape Rate. Within the rate hysteresis mode, if the intrinsic heart rate falls below the Hysteresis Escape Rate, the controller causes the heart to be paced at a pre-programmed Base Rate. In this regard, to afford the heart every opportunity to beat on its own, i.e., to allow atrial and ventricular muscle tissue to contract naturally without external stimulation pulses, the memory of the device stores a period of time, generally referred to as the "escape interval," that is slightly longer than the period of time between heart beats of a heart beating at a minimal acceptable rate. For example, if the heart is beating at a rate of 50 beats per minute, the time period between consecutive heart beats is 1200 milliseconds. Thus, if it is desired that the heart rate never slow to a rate less than 50 beats per minute, the escape interval of the pacemaker is set to an appropriate value that causes a stimulation pulse to always be generated if more than 1200 milliseconds elapse since the last heart beat. If a heart beat occurs before 1200 milliseconds have elapsed, then the heart is beating at a rate faster than 50 beats per minute, and no stimulation pulse need be generated. Upon sensing such an intrinsic heart beat within the allotted time period, the escape interval is reset, and a new escape interval is started. A stimulation pulse is generated at the conclusion of this new escape interval unless a intrinsic heart beat is again sensed during the escape interval. In this way, stimulation pulses are generated "on demand," i.e., only when needed, in order to maintain the heart rate at a rate that never drops below the rate set by the escape interval. Further information regarding rate hysteresis is provided within U.S. Pat. No. 5,237,992 to Poore, issued Aug. 24, 1993, entitled "Implantable Pacemaker Providing Hysteresis In Dual-Chamber Modes," which is incorporated by reference herein.

In the vasovagal syncope prevention mode, if the intrinsic heart rate falls below the Hysteresis Escape Rate, the controller causes the heart to be paced at a Vasovagal Syncope Response Rate, which is greater than the Base Rate. As will be further described below, the Vasovagal Syncope Response Rate is preferably set sufficiently high to offset the drop in blood pressure associated with vasovagal syncope to thereby prevent loss of consciousness by the patient. The device may also be programmed to use neither the rate hysteresis mode nor the vasovagal syncope mode and to instead use any other appropriate pacing mode, such as a non-hysteresis demand pacing mode wherein a pacing pulse is delivered on demand whenever an intrinsic beat is not detected within an escape interval set based on the Base Rate.

Figure 2:
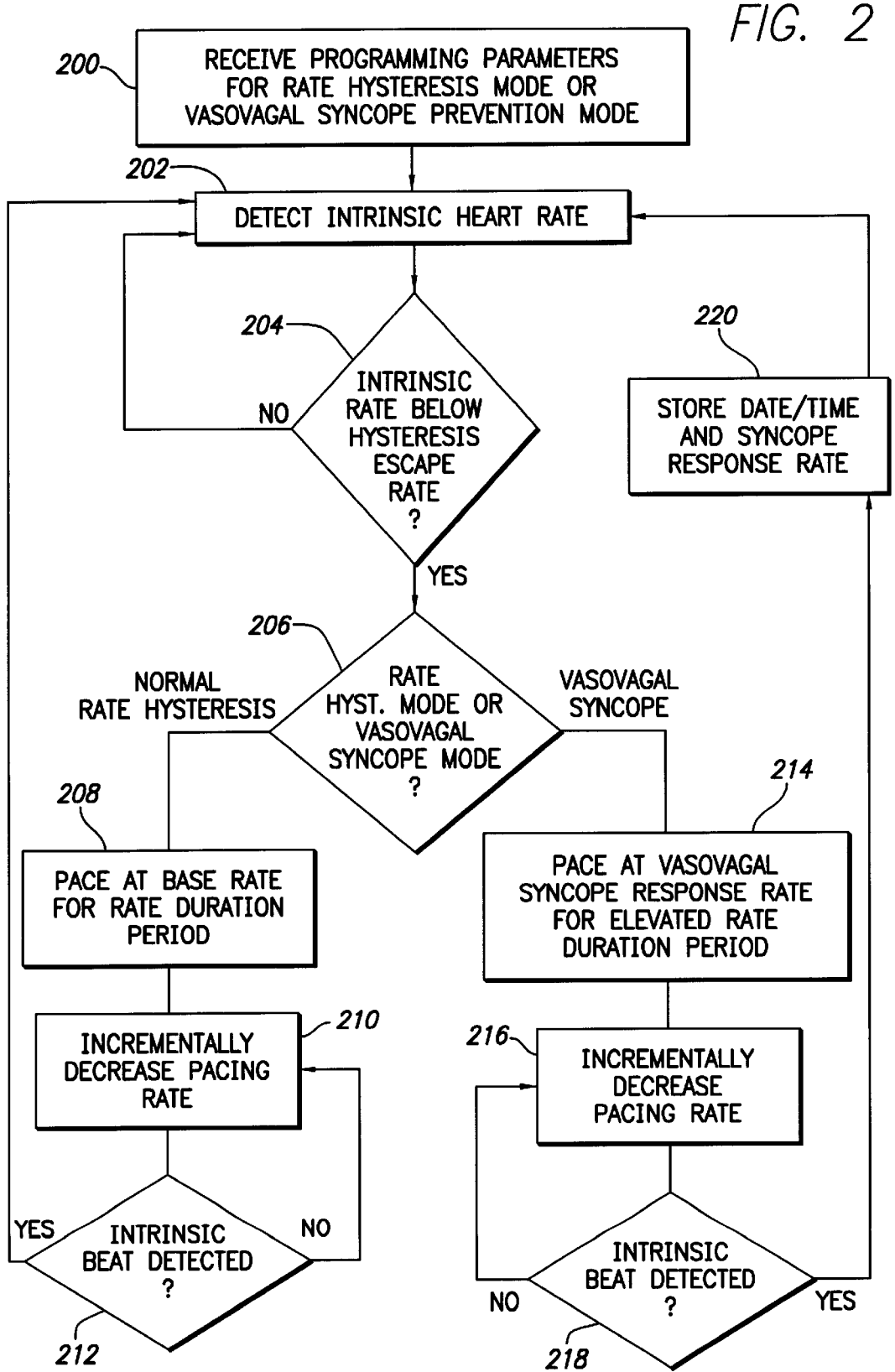
FIG. 2 is a flow chart illustrating steps performed by a controller of the device of FIG. 1 for implementing the vasovagal syncope prevention mode.

FIG. 2 illustrates, at a high level, the operation of controller 60 as it pertains to the rate hysteresis mode and the vasovagal syncope prevention mode. In the flow chart, the various steps performed by the controller are summarized in individual "blocks". Where a microcontroller (or equivalent) is employed, the flow chart presented herein provides the basis for a "control program" that may be used by such a microcontroller (or equivalent) to effectuate the desired control of the stimulation device. Those skilled in the art may readily write such a control program based on the flow charts and other descriptions presented herein. Also, those skilled in the art may readily modify the system described in the above-referenced patent to Poore to provide both the rate hysteresis mode and the vasovagal syncope prevention mode.

Now considering FIG. 2 in greater detail, the figure illustrates a pacing technique, which may be employed by controller 60 of FIG. 1 for prevention of vasovagal syncope. Initially, at step 200, controller 60 receives rate hysteresis programming commands from an external programmer device (not shown). The rate hysteresis commands specify a Base Rate and a Hysteresis Escape Rate either directly or in terms of other parameters from which the Base Rate and Hysteresis Escape Rate may be calculated. The programming commands also specify whether the controller is to be programmed into a vasovagal syncope prevention mode or a rate hysteresis mode. If programmed within the vasovagal syncope prevention mode, the programming commands may specify a Vasovagal Syncope Response Rate, which is higher than the Base Rate. Exemplary programmable rates are as follows: Hysteresis Escape Rate of 50 beats per minute (BPM), Base Rate of 60 BPM, and Vasovagal Syncope Response Rate of 80 BPM. As we described below, rather than providing a preprogrammed Vasovagal Syncope Response Rate, the controller may calculate Vasovagal Syncope Response Rate based upon preceding heart rate. In addition to the programmable rates, the controller also receives other hysteresis parameters including parameters specifying a rate decrement used to decrease the stimulation rate once the response time has elapsed. These and other parameters are stored by controller 60 within memory 94.

Beginning at block 202, the controller sets the escape interval by taking the reciprocal of the Programmed Base Rate. At block 204, a branch is executed as follows: if the escape interval times out and the controller triggers a pacing event at the end of the escape interval, then the device continues pacing at the Programmed Base rate, otherwise an intrinsic event is detected and the pacemaker is inhibited. This inhibition triggers the controller to transition to block 206 in which the escape interval is reset using the Reciprocal of the Hysteresis Rate. This rate is lower than the Programmed Base Rate and therefore the escape interval is longer than the escape interval calculated from the reciprocal of the Programmed Base Rate. If the pacemaker is inhibited by intrinsic events at block 204, then the device continues operation at the Hysteresis Rate as represented in block 206, otherwise the cardiac intrinsic rate is below the Hysteresis Rate and the pacemaker must pace the heart at the Hysteresis Escape Interval which is the reciprocal of the Hysteresis Escape Rate.

To prevent triggering a mode switch on just one event, this embodiment preferably triggers a test to determine if pacing at the Hysteresis Escape Interval has occurred one or more times, as represented by block 208. For example, one, two or more pacing events but typically less than eight pacing events may be used to trigger transition to increase the stimulation rate. These events may be consecutive pacing events or the sum total of pacing events.

The transition to a higher rate is dependent on whether the device is programmed to operate in the Vasovagal Syncope Prevention Mode or in the Standard Rate Hysteresis Mode. A branch is made, in block 210, based on the predetermined programming of the response mode. If Standard Rate Hysteresis is the programmed mode of operation, the device transitions to the Programmed Base Rate and continues operation starting in block 202.

If Vasovagal Syncope Prevention mode is the programmed mode of operation, the controller begins to pace the heart at the higher Vasovagal Syncope Response Rate for a preprogrammed Elevate Rate Duration Period time as represented by block 212. This response time may be programmed as a defined number of cardiac cycles or as a predefined time period. After the response time expires the controller advances to step 214, where the controller incrementally decreases the stimulation rate using the aforementioned decrement value until the Programmed Base Rate is reached. The vasovagal episode has been remedied and before returning to the Base Rate in block 202, the controller stores information identifying the syncope episode within memory 94 for subsequent review by the physician. To this end, the controller stores at least the date and time and syncope response rate if other than the preprogrammed rate.

As noted, the controller may use either a preprogrammed vasovagal syncope response rate or may calculate a vasovagal response rate based on the average ventricular intrinsic rate. To this end, the controller measures the average peak heart rate by storing the heart intervals and taking the reciprocal to calculate the rate and applying moving average to the last 2 to 10 intervals to estimate the peak average heart rate. The intervals are defined as the time intervals between consecutive ventricular sensed events, consecutive ventricular paced events, ventricular paced to sensed events, or ventricular sensed to paced events. Using the last minute or the last sixty-four events, the controller is constantly updating the peak average rate and storing the rate in memory 94. Then at step 212, the controller identifies the most recent average peak ventricular rate stored in memory 94 and adds a physician selectable programmable offset of 10, 20 or 30 ppm to the average peak ventricular rate. This establishes pacing at the Vasovagal Response Rate for a physician selectable Elevated Rate Duration Period, typically programmable from 15 seconds to 5 minutes. Alternatively, the Vasovagal Response Rate need not be based on the recent average peak ventricular rate, but may be one of several programmable fixed incremental offsets, for instance, 10, 20, 30 or 40 ppm above the programmed Base Rate. For instance, if the Base Rate is 60 ppm and of the rate incremental offset is chosen to be 40, the pacemaker will commence pacing at 100 ppm at step 212. In the controller 60 is programmed with a maximum vasovagal syncope response that that is higher than the maximum sensor rate (MSR) or higher than the maximum track rate (MTR), the vasovagal response rate is set to be no greater than the MTR or the MSR. Further information about the MSR and MTR is provided in the U.S. Pat. No. 5,269,299 to Poore et al, issued Dec. 14, 1993, entitled "System And Method For Preventing Atrial Competition During Sensor-Driven Operation Of A Dual-Chamber Pacemaker", which is incorporated by reference herein.

Recover to Base Rate is achieved in block 216, in this block the controller increments the escape interval to achieve the base rate. The increments may be chosen so as to decrement the rate by 2.5 ppm per cardiac cycle. This allows slowing to the Base Rate to occur over a duration of a few seconds to 20 second depending on the Vasovagal Response Rate. A slower recovery rate of 1 ppm per cardiac cycle or a faster recovery rate of 5 ppm per cardiac cycle would also be acceptable and are not necessarily critical to the performance of the algorithm for preventing Vasovagal Syncope events.

Preferably, patients subject to recurrent vasovagal syncope have their pacemaker or ICD programmed to the vasovagal syncope mode which paces at the elevated Vasovagal Syncope Response Rate in the event the intrinsic rate falls below the Hysteresis Escape Rate. By providing an elevated Vasovagal Syncope Response Rate for those patients prone to vasovagal syncope, the blood pressure of the patient is thereby prevented from dropping as much as would otherwise occur if pacing occurred only at the Hysteresis Escape Rate. As noted above, it is particularly critical for patients subject to vasovagal syncope that the blood pressure not be permitted to drop to the point where the patient may become unconscious. If pacing were to occur at only the Base Rate, the stimulation rate may not be sufficient to prevent blood pressure from dropping too far. Of course, the fact that the intrinsic rate drops below the Hysteresis Escape Rate does not necessarily mean that the patient is suffering from vasovagal syncope, rather it may be indicative of an episode of bradycardia. Nevertheless, given the risks associated with loss of consciousness, it is often better to switch to the higher syncope Vasovagal Syncope Response Rate rather than at the Base Rate for patients prone to vasovagal syncope. In any case, the physician makes the decision as to whether to set the pacemaker or ICD to the vasovagal mode, the rate hysteresis mode or some other preprogrammed mode such as a normal demand-based mode.

While the above description applies to a device having both a rate hysteresis pacing mode and a vasovagal syncope prevention mode, it is recognized that the vasovagal syncope prevention mode can be employed in devices that do not have a rate hysteresis pacing mode without departing from the spirit of the invention. One of skill in the art could readily delete the rate hysteresis pacing mode blocks from the flow chart shown in FIG. 2.

In another embodiment, the stimulation device can operate in either a rate hysteresis pacing mode or a vasovagal syncope prevention mode as determined by an appropriate "vasovagal detecting syncope" sensor for detecting a non-rate-based parameter, such as a hemodynamic or position sensor corresponding to vasovagal syncope, hereinafter simply a "physiologic sensor".

One such hemodynamic sensor is a blood pressure sensor for detecting a sudden drop in blood pressure. Blood pressure sensors are well known, see for example U.S. Pat. No. 5,615,684 (Hagel, et. al), which patent is hereby incorporated herein by reference.

Another such hemodynamic sensor is an impedance sensor which may be used to detect a sudden drop in blood filling. A sudden drop in impedance of blood filling the heart, particularly if it is accompanied by a slowing of the heart rate, would also be a indication of vasovagal syncope. Impedance sensors are well known, see for example, in U.S. Pat. No. U.S. Pat. No. 4,535,774 of Olson, which patent is also hereby incorporated herein by reference. As such, in FIG. 1, the device may include an impedance measuring circuit 120 which is enabled by the microcontroller 60 by a control signal 122.

Contractility may further be a physiological parameter that would indicate that circulating catecholamines desire an increase in heart rate, contrary to the vagus nerve signals. Contractility signals may be obtained by measuring ventricular gradient, also known as post-depolarization integral, as is known in the art. For a complete description of the ventricular gradient, see U.S. Pat. No. 4,955,376 (Callaghan, et. al), which patent is also hereby incorporated herein by reference.

Yet in another embodiment, the physiological sensor 110 may take the form of a posture sensor to detect when the patient has fainted (suddenly in a supine position) due to vasovagal syncope. Accordingly, an activity sensor, such as an accelerometer may be mounted within the housing 40 of the stimulation device 10 and used to detect upright or supine posture. The activity sensor may further be used to detect sleep mode by measuring activity variance. Activity variance and sleep mode are fully described in U.S. Pat. No. 5,010,893 (Sholder) and U.S. Pat No. 5,865,760 (Lidman, et. al), which patents are hereby incorporated herein by reference.

Accordingly, any sensor may be used which is capable of sensing a physiological parameter, which corresponds to the vasovagal syncope. While shown as being included within the stimulation device 10, it is to be understood that the physiologic sensor 110 may also be external to the stimulation device 10 (i.e. on the lead), yet still be implanted within or carried by the patient.

As such, the device 10 may determine whether the patient has vasovagal syncope based solely on such a physiologic sensor 110. Alternatively, the physiologic sensor 110 may be used in combination with a rate detecting technique, such as the one described above in which the rate must drop below the Hysteresis Escape Rate, or any such rate drop detecting technique.

After one or more such events, the device 10 may automatically re-program the mode in memory 94 to the vasovagal syncope prevention mode so that at block 210, the device remains in this mode. In this instance, the device 10 would continuously operate in blocks 202, 204, 206, 208, 210, 212, 214, and 216. The vasovagal syncope detecting circuitry may then be disabled, since it is presumed that after one or more episodes, the patient is more likely to need this mode rather than the rate hysteresis mode, and the response time can be slightly faster without this detector.

In yet one other embodiment, the physiologic sensor 110 may indicate that the patient is not in a vasovagal syncope state. Accordingly, the device 10 may automatically re-program the mode in memory 94 to the rate hysteresis pacing mode so that at block 210, the device remains in this mode. In this instance, the device 10 would continuously operate in blocks 202, 204, 206, 208 and 210.

In yet one more embodiment, the physiological sensor may be used for sensing when the patient is at a hemodynamically appropriate rate. Accordingly, the microcontroller 60 includes control circuitry to determine an appropriate Vasovagal Syncope Response Rate based on a value of the physiologic sensor 110.

Hence, vasovagal syncope response is provided using a relatively minor modification to the conventional rate hysteresis algorithm. This is in contrast with many conventional vasovagal syncope detection and prevention techniques which may require complex algorithms to analyze the intrinsic heart rate as a function of time to determine the onset of vasovagal syncope. As noted, by the time such devices have determined whether vasovagal syncope might be occurring, the blood pressure of the patient has probably already dropped too far such that any increase in stimulation rate will likely be insufficient to prevent loss of consciousness.

What have been described are techniques for preventing vasovagal syncope within patients subject to recurrent vasovagal syncope using an implanted cardiac stimulation device. Principles of the invention are applicable to other types of syncope as well such as other types of neurocardiogenic syncope. Thus, the specific examples herein are intended merely to be illustrative of the invention and should not be construed as limiting the scope of the invention.

What is claimed is:

1. An implantable cardiac stimulation device, comprising:
   a programmable Base Rate, a Hysteresis Escape Rate below the Base Rate, and a Vasovagal Syncope Response Rate above the Base Rate;
   a pulse generator to generate stimulation pulses at one of the Base Rate, the Hysteresis Escape Rate, and the Vasovagal Syncope Response Rate based on a mode of operation;
   a vasovagal syncope detecting sensor to detect a non-rate-based parameter corresponding to vasovagal syncope; and
   a controller to operate in a Vasovagal Syncope mode when the non-rate-based parameter indicates that vasovagal syncope is present, wherein the rate of stimulation pulses are immediately adjusted to the Vasovagal Syncope Response Rate when the non-rate-based parameter indicates that vasovagal syncope is present.

2. The stimulation device of claim 1, further comprising:
   a sensor to sense ventricular cardiac signals and to determine an intrinsic ventricular heart rate;
   a rate detector to detect a sudden drop in the intrinsic heart rate as a secondary indication of vasovagal syncope;
   wherein the controller operates in the Vasovagal Syncope mode when the rate detecting means confirms the occurrence of vasovagal syncope, wherein the controller selectively extends a minimum stimulation pulse escape interval by adding a prescribed hysteresis value upon sensing a ventricular cardiac signal to produce a Hysteresis Escape Rate below the Base Rate, and wherein the controller determines when the intrinsic rate falls below the Hysteresis Escape Rate.

3. The stimulation device of claim 2, wherein the controller disables the vasovagal detecting syncope sensor upon detecting at least one episode of vasovagal syncope, and wherein the controller operates in the Vasovagal Syncope mode for each subsequent detection of a sudden drop in the intrinsic heart rate.

4. The stimulation device of claim 2, wherein the rate detector comprises:
   a hysteresis mode to selectively extend a minimum stimulation pulse escape interval by adding a prescribed hysteresis value upon sensing a ventricular cardiac signal to produce a Hysteresis Escape Rate below the Base Rate; and
   wherein the controller determines when the intrinsic rate falls below the Hysteresis Escape Rate.

5. The stimulation device as of claim 4, wherein the controller controls the rate of stimulation pulses to the heart in a Hysteresis Rate mode when the intrinsic heart rate falls below the Hysteresis Escape Rate and the vasovagal detecting syncope sensor determines the absence of vasovagal syncope.

6. An implantable cardiac stimulation device comprising:
   means for defining a programmable Base Rate, a Hysteresis Escape Rate below the Base Rate, and a Vasovagal Syncope Response Rate above the Base Rate;
   pulse generating means for generating stimulation pulses at one of the Base Rate, the Hysteresis Escape Rate, and the Vasovagal Syncope Response Rate based on a mode of operation;
   vasovagal syncope detecting means for detecting a non-rate-based parameter corresponding to vasovagal syncope; and
   control means for operating in a Vasovagal Syncope mode whenever the non-rate-based parameter indicates that vasovagal syncope is present, wherein the rate of stimulation pulses are immediately adjusted to the Vasovagal Syncope Response Rate whenever the non-rate-based parameter indicates that vasovagal syncope is present.

7. The stimulation device as of claim 6, wherein the vasovagal syncope detecting means comprises means for detecting when a patient has lost consciousness.

8. The stimulation device as of claim 7, wherein the means for detecting when the patient has lost consciousness comprises a posture sensor capable of detecting when the patient is one of upright or supine.

9. The stimulation device as of claim 2, wherein the vasovagal syncope detecting means comprises means for predicting when the patient may lose consciousness comprising a blood pressure sensor capable of detecting a sudden drop in blood pressure corresponding to hypotension.

10. The stimulation device as of claim 7, wherein the vasovagal syncope detecting means comprises means for predicting when the patient may lose consciousness comprising an impedance pressure sensor capable of detecting that the patient has had a sudden drop in blood filling in the ventricle.

11. The stimulation device as of claim 7, wherein the vasovagal syncope detecting means comprises means for predicting when the patient may lose consciousness comprising a contractility sensor capable of detecting a sudden need for an increase in stimulation rate.

12. The stimulation device as of claim 7, further comprising:
    physiological sensing means for sensing when the patient is at a hemodynamically appropriate rate; and
    wherein the control means further comprises means for determining the Vasovagal Syncope Response Rate based on the physiologic sensing means.

13. The stimulation device as of claim 6, further comprising:
    sensing means for sensing ventricular cardiac signals and for determining an intrinsic ventricular heart rate; and
    rate detecting means for detecting a sudden drop in the intrinsic heart rate as a secondary indication of vasovagal syncope;
    wherein the control means further comprises means for operating in the Vasovagal Syncope mode when the rate detecting means confirms the occurrence of vasovagal syncope.

14. An implantable cardiac stimulation device comprising:
    means for defining a programmable Base Rate, a Hysteresis Escape Rate below the Base Rate, and a Vasovagal Syncope Response Rate above the Base Rate;

pulse generating means for generating stimulation pulses at one of the Base Rate, the Hysteresis Escape Rate, and the Vasovagal Syncope Response Rate based on a mode of operation;

vasovagal syncope detecting means for detecting a non-rate-based parameter corresponding to vasovagal syncope;

control means for operating in a Vasovagal Syncope mode whenever the non-rate-based parameter indicates that vasovagal syncope is present, wherein the rate of stimulation pulses are adjusted to the Vasovagal Syncope Response Rate;

sensing means for sensing ventricular cardiac signals and for determining an intrinsic ventricular heart rate;

rate detecting means for detecting a sudden drop in the intrinsic heart rate as a secondary indication of vasovagal syncope;

wherein the control means further comprises means for operating in the Vasovagal Syncope mode when the rate detecting means confirms the occurrence of vasovagal syncope; and means for disabling the vasovagal syncope detecting means upon detecting at least one episode of vasovagal syncope and for operating in the Vasovagal Syncope mode for each subsequent detection of a sudden drop in the intrinsic heart rate.

15. An implantable cardiac stimulation device comprising:

means for defining a programmable Base Rate, a Hysteresis Escape Rate below the Base Rate, and a Vasovagal Syncope Response Rate above the Base Rate;

pulse generating means for generating stimulation pulses at one of the Base Rate, the Hysteresis Escape Rate, and the Vasovagal Syncope Response Rate based on a mode of operation;

vasovagal syncope detecting means for detecting a non-rate-based parameter corresponding to vasovagal syncope;

control means for operating in a Vasovagal Syncope mode whenever the non-rate-based parameter indicates that vasovagal syncope is present, wherein the rate of stimulation pulses are adjusted to the Vasovagal Syncope Response Rate;

sensing means for sensing ventricular cardiac signals and for determining an intrinsic ventricular heart rate;

rate detecting means for detecting a sudden drop in the intrinsic heart rate as a secondary indication of vasovagal syncope;

wherein the control means further comprises means for operating in the Vasovagal Syncope mode when the rate detecting means confirms the occurrence of vasovagal syncope; and hysteresis means for selectively extending a minimum stimulation pulse escape interval by adding a prescribed hysteresis value upon sensing a ventricular cardiac signal to produce a Hysteresis Escape Rate below the Base Rate; and means for determining when the intrinsic rate falls below the Hysteresis Escape Rate.

16. The stimulation device as of claim 15, wherein the control means further comprises:

means for controlling the rate of stimulation pulses to the heart in a Hysteresis Rate mode whenever the intrinsic heart rate falls below the Hysteresis Escape Rate and the vasovagal syncope detecting means determines the absence of vasovagal syncope.

17. The stimulation device as of claim 16, wherein the control means further comprises:

inhibiting means, when operating in the Hysteresis Rate mode, for inhibiting the generation of stimulation pulses when the intrinsic ventricular heart rate falls below the Base Rate but above the Hysteresis Escape Rate, and for triggering the generation of stimulation pulses at the Base Rate whenever the intrinsic heart rate falls below the Hysteresis Escape Rate.

18. The stimulation device as of claim 16, further comprising:

means for disabling the Hysteresis Rate mode upon detecting at least one episode of vasovagal syncope.

19. A method to stimulate a heart of a patient using an implantable cardiac stimulation device, the method comprising:

defining a programmable Base Rate, a Hysteresis Escape Rate below the Base Rate, and a Vasovagal Syncope Response Rate above the Base Rate;

generating stimulation pulses at one of the Base Rate, the Hysteresis Escape Rate, and the Vasovagal Syncope Response Rate based on a mode of operation;

detecting a non-rate-based parameter corresponding to vasovagal syncope; and operating in a Vasovagal Syncope mode when the non-rate-based parameter indicates that vasovagal syncope is present, wherein the rate of stimulation pulses are immediately adjusted to the Vasovagal Response Rate when the non-rate-based parameter indicates that vasovagal syncope is present.

20. The method of claim 19, further comprising:

sensing ventricular cardiac signals and determining an intrinsic ventricular heart rate; and detecting a sudden drop in the intrinsic heart rate as a secondary indication of vasovagal syncope;

wherein the operating in a Vasovagal Syncope mode further comprises operating in the Vasovagal Syncope mode when detecting a sudden drop in the intrinsic heart rate.

21. The method of claim 20, further comprising disabling the detecting a non-rate-based parameter upon detecting at least one episode of vasovagal syncope and operating in the Vasovagal Syncope mode for each subsequent detection of a sudden drop in the intrinsic heart rate.

22. The method of claim 20, wherein the detecting a sudden drop in the intrinsic heart rate comprises:

selectively extending a minimum stimulation pulse escape interval by adding a prescribed hysteresis value upon sensing a ventricular cardiac signal to produce a Hysteresis Escape Rate below the Base Rate; and determining when the intrinsic rate falls below the Hysteresis Escape Rate.

* * * * *